United States Patent [19]
Fuller et al.

[11] Patent Number: 4,765,179
[45] Date of Patent: Aug. 23, 1988

[54] RADIO FREQUENCY SPECTROSCOPY APPARATUS AND METHOD USING MULTIPLE FREQUENCY WAVEFORMS

[75] Inventors: Milton E. Fuller, Reno, Nev.; Gary S. Fletcher, Jr., Carmichael, Calif.

[73] Assignee: Solid State Farms, Inc., Reno, Nev.

[21] Appl. No.: 22,973

[22] Filed: Mar. 6, 1987

Related U.S. Application Data

[63] Continuation-in-part of Ser. No. 774,150, Sep. 9, 1985, Pat. No. 4,679,426.

[51] Int. Cl.$^4$ ............................................. G01N 29/02
[52] U.S. Cl. ........................................ 73/53; 73/61 R
[58] Field of Search .................... 73/53, 61 R, 61.1 R, 73/590

[56] References Cited

U.S. PATENT DOCUMENTS

| | | |
|---|---|---|
| 3,048,772 | 8/1962 | Saunders et al. |
| 3,051,896 | 8/1962 | Bieganski |
| 3,265,967 | 8/1966 | Heald |
| 3,287,638 | 11/1966 | Bolie |
| 3,489,522 | 1/1970 | McConnell |
| 3,648,513 | 3/1972 | Patterson ............................. 73/53 |
| 3,654,072 | 4/1972 | Massa ............................... 73/53 X |
| 3,765,841 | 10/1973 | Paulson et al. |
| 3,866,118 | 2/1975 | Ghosh et al. |
| 4,094,304 | 6/1978 | Wright, Jr. |
| 4,104,585 | 8/1978 | Schofield |
| 4,110,686 | 8/1978 | Leskovar et al. |
| 4,135,131 | 1/1979 | Larsen et al. |
| 4,257,001 | 3/1981 | Partain et al. |
| 4,327,587 | 5/1982 | Docekal et al. ..................... 73/590 |
| 4,344,440 | 8/1982 | Aaby et al. |
| 4,364,008 | 12/1982 | Jacques |
| 4,488,559 | 12/1984 | Iskander |
| 4,531,526 | 7/1985 | Genest |

OTHER PUBLICATIONS

Afsar, et al., "The Measurement of the Properties of Materials," *Proceedings of the IEEE*, vol. 74, No. 1, pp. 183-199 (Jan., 1986).

Gestblom, et al., "The Single Reflection Method in Dielectric Time Domain Spectroscopy," *The Journal of Physical Chemistry*, vol. 88, No. 4, pp. 664-666 (1984).

Gabriel, et al., "Comparison of the Single Reflection and Total Reflection TDS Techniques," *J. Phys. E. Sci. Instrum.*, vol. 17, pp. 513-516 (1984).

Mopsik, "Precision Time-Domain Dielectric Spectrometer," *Rev. Sci. Instrum.*, vol. 55, No. 1, pp. 79-87 (Jan. 1984).

*Primary Examiner*—Michael J. Tokar
*Assistant Examiner*—Joseph W. Roskos
*Attorney, Agent, or Firm*—Flehr, Hohbach, Test, Albritton & Herbert

[57] ABSTRACT

An apparatus and method for measuring the concentration of a chemical substance in a test sample based on a technique of waveform distortion analysis is disclosed. The apparatus includes a waveform generator that generates a periodic electromagnetic signal having a plurality of frequencies simultaneously present. Preferably the signal has a fundamental frequency and simultaneously present harmonic frequencies which shape the waveform. The shaped periodic signal is transmitted through the test sample by a probe assembly which also receives the transmitted signal from the test sample. Propagation of the shaped signal through the test sample results in a change in the waveform shape or distortion by the chemical, and a detector circuit is provided that quantifies the change in shape of the signal to determine the concentration of the chemical in the test sample. The harmonics producing the waveform shape and the fundamental frequency of the signal are both selected so that the change in shape of the signal is particularly responsive to the presence of a selected chemical substance. The magnitude of the distortion or change in shape of the signal can be directly correlated to the concentration of the selected chemical substance.

17 Claims, 4 Drawing Sheets

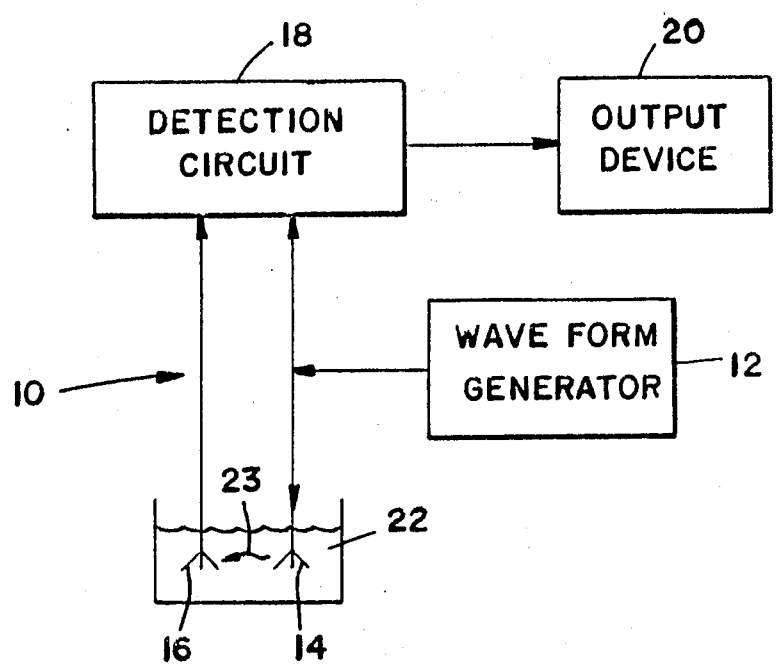
FIG_1
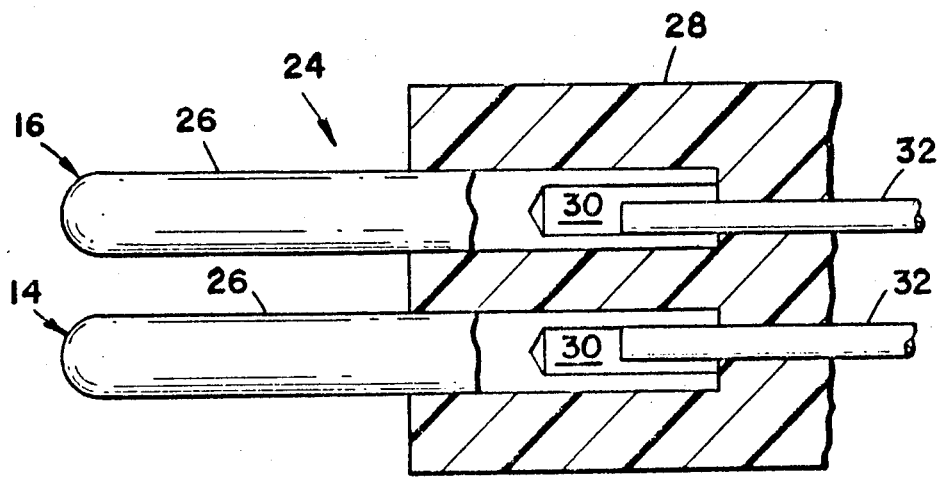
FIG_2

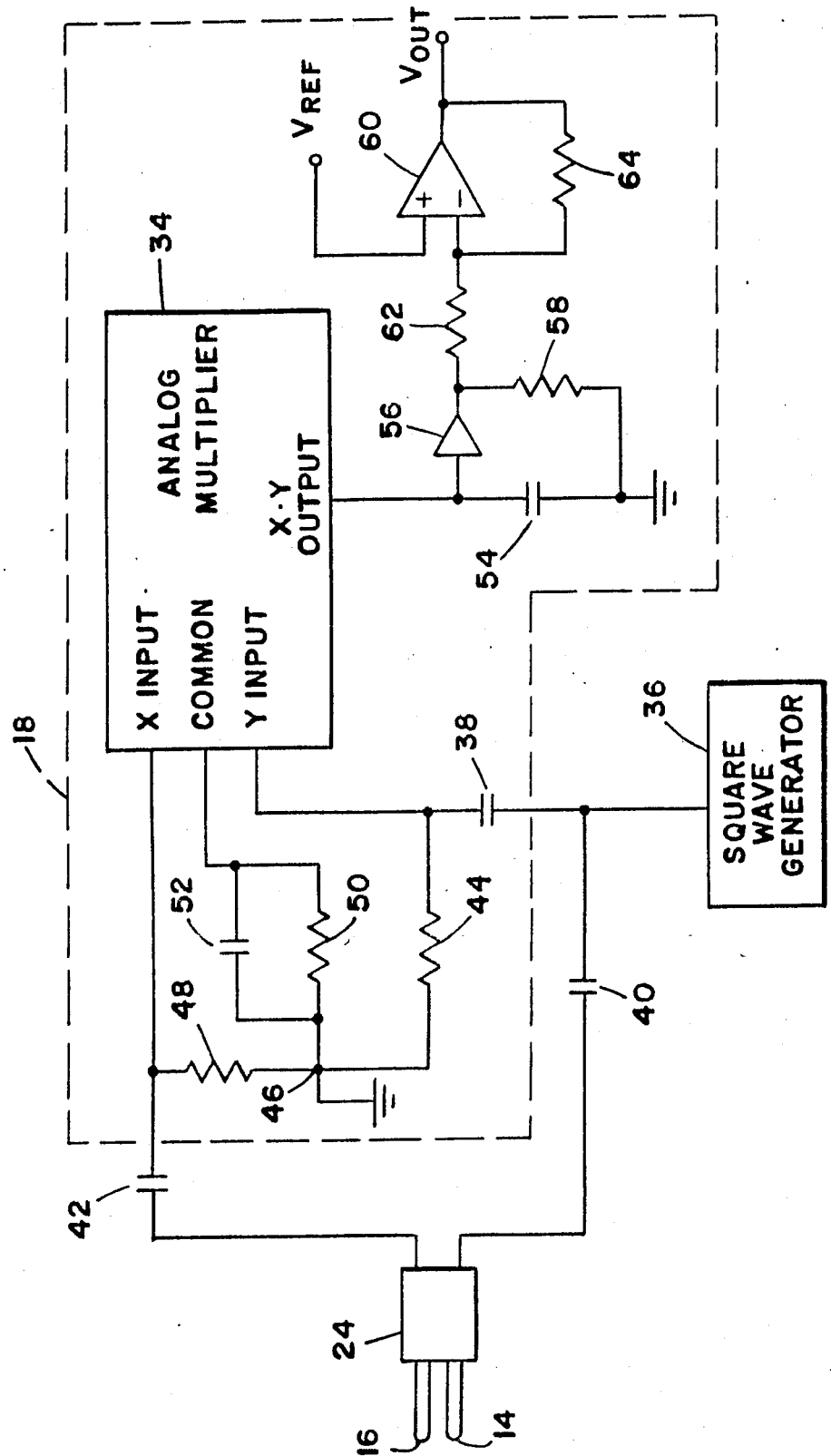
FIG_3

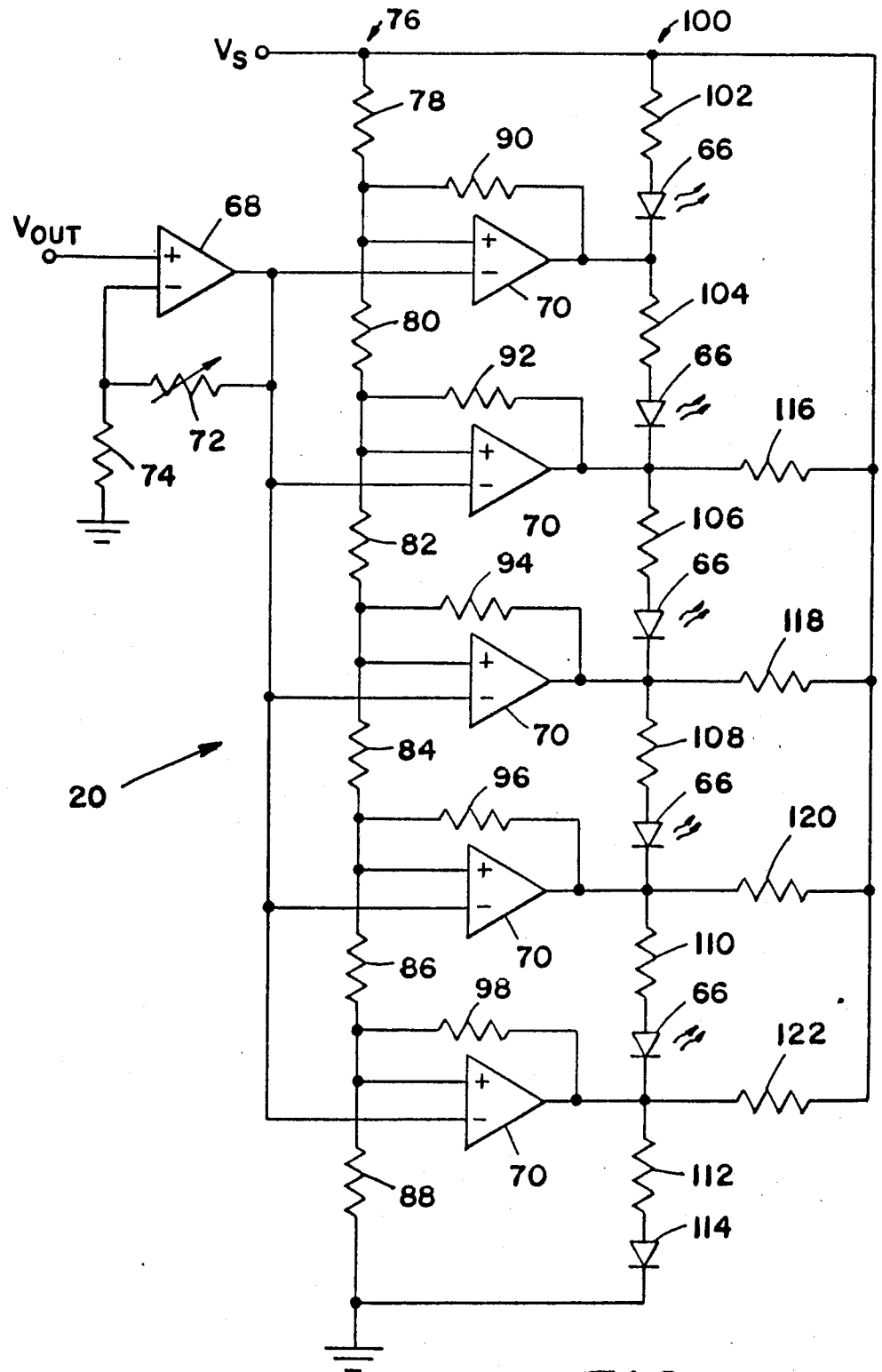
FIG_4

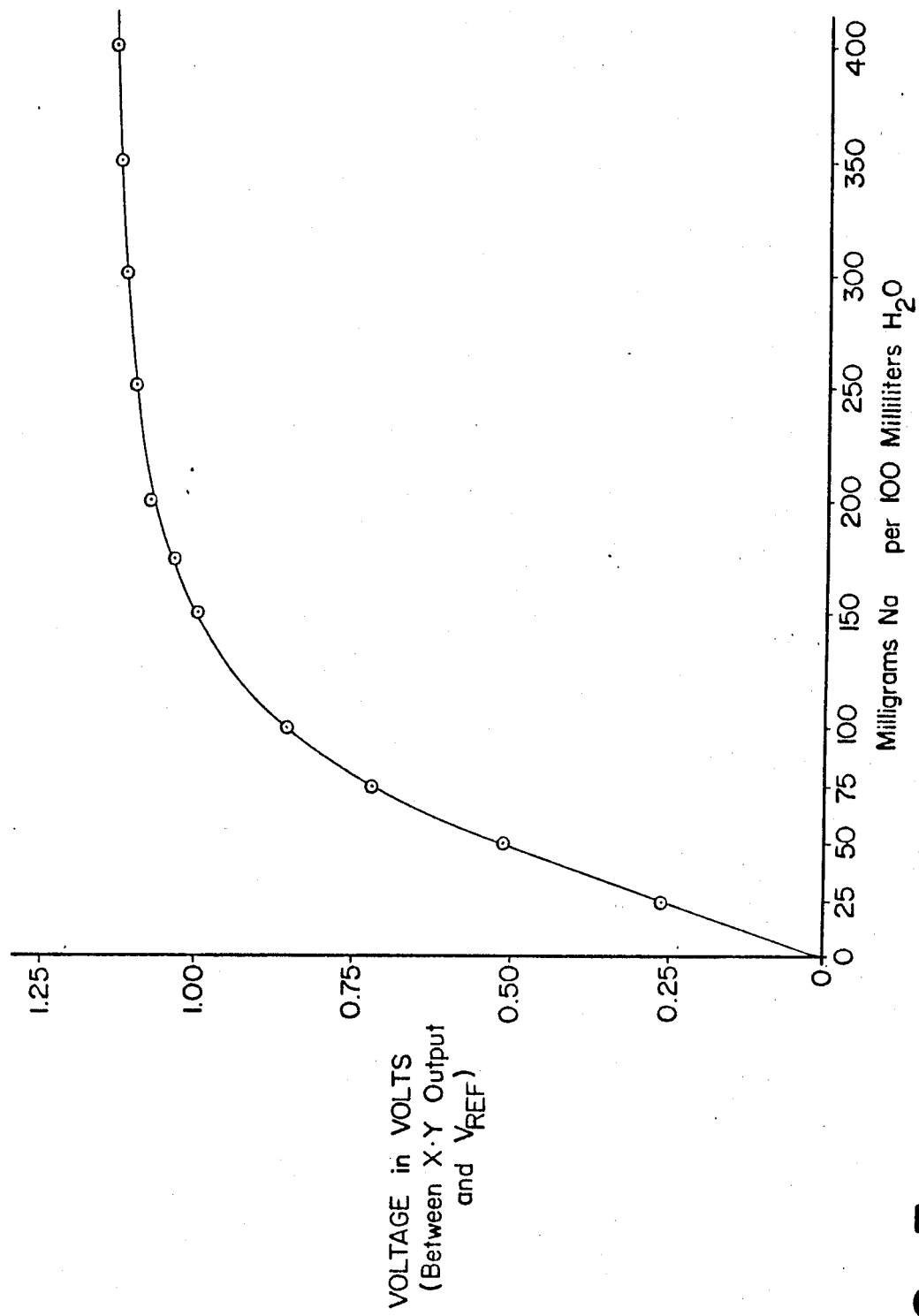
FIG_5

RADIO FREQUENCY SPECTROSCOPY APPARATUS AND METHOD USING MULTIPLE FREQUENCY WAVEFORMS

This application is a continuation-in-part application based upon co-pending application Ser. No. 774,150, filed Sept. 9, 1985, entitled "WAVE SHAPE CHEMICAL ANALYSIS APPARATUS AND METHOD" and now U.S. Pat. No. 4,679,426.

TECHNICAL FIELD

This invention relates generally to radio frequency spectroscopy, and more particularly, relates to the transmission of electromagnetic signals, preferably in the radio frequency range, through a specimen to enable a determination of the presence and/or concentration of a chemical in the specimen.

BACKGROUND ART

The ability to measure the concentration of a chemical in a test specimen or sample, and particularly the ability to measure a single chemical in a test specimen containing a complex mixture of chemicals, has numerous applications. Obviously, standard chemical analysis techniques are capable of such determinations, but they tend to have many disadvantages. In recent years, therefore, considerable effort has been directed toward the determination of various properties of materials using sound and electromagnetic waves or one-shot pulses as the basis for analysis. Such wave and pulse based techniques often have an inherent advantage over conventional chemical analysis, namely, the ability to effect a non-invasive in vivo analysis.

Two typical examples of chemical analyses in the health area alone which are of considerable interest today are: the analysis of the sodium content of food and the analysis of glucose content in blood. In both instances the material being analyzed is relatively complex in nature and presents substantial problems in connection with discriminating between the chemical being tested for and similar chemicals present in the sample, which similar chemicals may mask or alter the results of the analysis. Moreover, in connection with any blood glucose analysis, it is highly desirable to accomplish the analysis using a non-invasive technique.

There are a number of alternatives to traditional chemical processes which currently are available and are capable of measuring the concentration of a chemical substance, such as sodium, in a specimen, such as a food specimen. These apparatus include mass spectrophotometry apparatus, nuclear resonance devices, flame photometry apparatus, specific electrodes, conductivity testers, and refractometry devices. Unfortunately, the accuracy of these currently available apparatus is strongly dependent upon their cost. At the low end of the cost scale is the direct current conductivity tester, which measures the conductivity of a test sample to determine sodium content. Unfortunately, a continuity tester will yield inaccurately high test results when the test sample contains other conductive substances, such as vinegar. What is needed is an inexpensive and easy to use, but accurate, sodium measurement apparatus.

Similarly, blood-sugar analysis apparatus and methods are known which are reasonably accurate and can be used by patients themselves to determine their glucose levels. Such apparatus, however, heretofore have required invasive sampling by the patient, and produce results which will vary with the experience of the patient in using the apparatus. Thus, measurements by such patients are primarily valuable in determining relative changes in glucose levels, rather than the absolute value of the glucose level.

The use of sonic and electromagnetic waves and pulses as analytical tools has progressed considerably during the last twenty years. Sonic-based systems generally have depended upon the rate of propagation and/or the attenuation of sound in the test specimen. Electroacoustic transducers are used to transmit sound waves or pulses into the specimen and to receive the waves or pulses after transmission through the specimen. Various methods are employed to determine the rate of propagation of sound through the test specimen or to determine the change in amplitude (attenuation) of the sound transmitted through the specimen. Speed and/or attenuation are then compared to values for calibration specimens having a known amount of the chemical to be studied. Typical of such acoustic-based chemical analysis systems are the apparatus and methods set forth in U.S. Pat. Nos. 4,327,587, 3,654,072 and 3,648,513. An acoustic impedance apparatus also is disclosed in U.S. Pat. No. 4,094,304. The system employs acoustic energy pulses and detection of the echo pulses.

Acoustic-based chemical analysis systems, however, have generally been found to have a limited scope in terms of the compounds which may be studied. Moreover, they lack the ability to discriminate between chemicals as the test specimens become more complex in their make up. Such acoustic apparatus and methods, therefore, lack the precision and specificity which otherwise would be desirable in a chemical analysis system.

The use of electromagnetic waves and pulses in connection with the measurement and analysis of various chemical properties has been found to have various advantages. Such chemical analysis systems are often referred to as microwave spectroscopy techniques, although they may include frequency ranges which are considered by some as being in the radio frequency range.

The method and apparatus of the present invention employ a periodic shaped wave having a frequency which is preferably in about the one megahertz to about one gigahertz range. It is believed that the present method and apparatus may be found to be useful in frequency ranges which are generally accepted to be in the microwave range, i.e., above five hundred megahertz. Moreover, the present system also may be useful at frequencies below one megahertz. Accordingly, references to present invention in this application as being a "radio frequency" spectroscopy method and apparatus are for the sake of convenience only, not by way of limitation.

Microwave and radio frequency spectroscopy has been used extensively to measure the dielectric properties of materials and particularly permittivity. Among the techniques employed in connection with permittivity studies have been reflection, transmission and resonant methods. Guided and free-space systems and pulsed, single frequency and swept frequency range systems all have been studied and reported in the technical literature.

Perhaps the greatest amount of effort has been directed in the area of studying the reflection characteristics of electromagnetic pulses. A single electromagnetic pulse is transmitted down a waveguide to impinge against a target specimen, and the reflection of the pulse off the front and/or back surfaces of the specimen is studied. It is inherent, of course, that multiple reflection techniques using thin samples also have some effect of transmission present in the measurements. In connection with all of these studies, the resulting time delay, phase change and/or pulse attenuation are determined and correlated to permittivity.

The apparatus and method of the present invention are based upon the use of a periodic electromagnetic signal, while most of the time domain spectroscopy techniques reported in the technical literature employ an electromagnetic pulse. Pulse technology is based upon a one-shot or transient event (a voltage increase or decrease) in which one must wait for the system to respond to the event and collect data as to the response before initiating a second event. As used in this application, therefore, the expression "periodic" excludes transient event or one-shot systems (even one-shot systems in which a plurality of events are sequentially used to collect data) and includes waveforms which repeatedly return to a reference level at a frequency substantially faster than the minimum system response time associated with single pulse measurements.

Representative of one-shot or pulse permittivity studies are the following articles: Afsar, et al., "The Measurement of the Properties of Materials," *Proceedings of the IEEE*, Vol. 74, No. 1, pp. 183–199 (January, 1986); Gestblom, et al., "The Single Reflection Method in Dielectric Time Domain Spectroscopy," *The Journal of Physical Chemistry*, Vol. 88, No. 4, pp. 664–666 (1984); Gabriel, et al., "Comparison of the Single Reflection and Total Reflection TDS Techniques," *J. Phys. E: Sci. Instrum.*, Vol. 17, pp. 513–516 (1984); Mopsik, "Precision Time-Domain Dielectric Spectrometer," *Rev. Sci. Instrum.*, Vol. 55, No. 1, pp. 79–87 (January, 1984); Chahine, et al., "Drift Reduction of the Incident Signal in Time Domain Reflectometry," *Rev. Sci. Instrum.*, Vol. 54 (9), pp. 1243–46 (September, 1983); Boned, et al., "Automatic Measurements of Complex Permittivity (from 2MHz to 8GHz) Using Time Domain Spectroscopy," *J. Phys. E.: Sci. Instrum.*, Vol. 15, pp. 534–538 (1982); Gestblom, et al., "A Computer Controlled Dielectric Time Domain Spectrometer," *J. Phys. E: Sci. Instrum.*, Vol. 13, pp. 1067–1070 (1980); Parisien, et al., "A Microprocessor-Controlled Time-Domain Spectrometer," *IEEE Trans. on Inst. and Meas.*, Vol. IM-28, No. 4, pp. 269–272 (December, 1979); Dawkins, et al., "An On-line Computer-Based System for Performing Time Domain Spectroscopy I. Main Features of the Basic System," *J. Phys. E.: Sci. Instrum.*, Vol. 12, pp. 1091–1099 (1979); Gestblom, et al., "Transmission Methods in Dielectric Time Domain Spectroscopy," *The Journal of Physical Chemistry*, Vol. 81, No. 8, pp. 782–788 (1977); Gestblom, et al., "A New Transmission Method in Dielectric Time Domain Spectroscopy," *Chemical Physics Letters*, Vol. 47, No. 2, pp. 349–351 (April, 1977); Bottreau, et al., "On a Multiple Reflection Time Domain Method in Dielectric Spectroscopy: Application to the Study of Some Normal Primary Alcohols," *The Journal of Chemical Physics*, Vol. 66, No. 8, pp. 3331–3336 (April, 1977); Cole, "Time-Domain Spectroscopy of Dielectric Materials," *IEEE Trans. on Inst. and Meas.*, Vol. IM-25, No. 4, pp. 371–375 (December, 1976); Chahine, et al., "Measurements of Dielectric Properties by Time Domain Spectroscopy," *The Journal of Chemical Physics*, Vol. 65, No. 6, 2211–2215 (Sept., 1976); Claasen, et al., "Approximate Solutions in Multiple Reflection Time Domain Spectroscopy," *The Journal of Chemical Physics*, Vol. 63, No. 1, pp. 68–73; van Gemert, "Multiple Reflection Time Domain Spectroscopy. II. A Lumped Element Approach Leading to an Analytical Solution for the Complex Permittivity," *The Journal of Chemical Physics*, Vol. 62, No. 7, pp. 2720–2726 (April, 1975); Cole, "Evaluation of Dielectric Behavior by Time Domain Spectroscopy. I. Dielectric Response by Real Time Analysis," *The Journal of Physical Chemistry*, Vol. 79, No. 14, pp. 1459–1469 (1975); Cole, "Evaluation of Dielectric Behavior by Time Domain Spectroscopy. II. Complex Permittivity," *The Journal of Physical Chemistry*, Vol. 79, No. 14, pp. 1469–1474 (1975); Clark, et al., "Multiple Reflection Time Domain Spectroscopy," *Journal of Chemical Society*, Vol. 70, pp. 1847–1862 (1974); Rzepecka, et al., "A Lumped Capacitance Method for the Measurement of the Permittivity and Conductivity in the Frequency and Time Domain—A Further Analysis," *IEEE Trans. on Inst. and Meas.*, Vol. IM-24 No. 1, pp. 27–32 (March, 1975); Suggett, "Microwave Dielectric Measurements Using Time Domain Spectroscopy: Note on Recent Technique Advances," *J. Phys. E: Sci. Inst.*, Vol. 8, pp. 327–330 (1975); Springett, et al., "Thin Sample Time Domain Reflectometry for Nonideal Dielectrics," *Can. J. Phys.*, Vol. 52, pp. 2463–2468 (1974); van Gemert, "Evaluation of Dielectric Permittivity and Conductivity by Time Domain Spectroscopy. Mathematical Analysis of Fellner-Feldegg's Thin Cell Method," *J. Chem. Phys.*, Vol. 60, No. 10, pp. 3963–3974 (1974); Hines, et al., "Time-Domain Oscillographic Microwave Network Analysis Using Frequency-Domain Data," *IEEE Trans. on Microwave Theory and Techniques*, Vol. MTT-22, No. 3, pp. 276–282 (March, 1974); van Gemert, "High-Frequency Time-Domain Methods in Dielectric Spectroscopy," *Philips Res. Repts.*, Vol. 28, pp. 530–572 (1973); Bucci, et al., "Time-Domain Techniques for Measuring the Conductivity and Permittivity Spectrum of Materials," *IEEE Trans. on Inst. and Meas.*, Vol. IM-21, No. 3, pp. 237–243 (August, 1972); Nicholson, et al., Measurement of the Intrinsic Properties of Materials by Time-Domain Techniques," *IEEE Trans. on Inst. and Meas.*, Vol. IM-19, No. 4, pp. 377–382 (November, 1970); Hyde, "Wide-Frequency-Range Dielectric Spectrometer," *Proc. Inst. Elect. Eng.*, Vol. 117, pp. 1891–1901 (1970); Fellner-Feldegg, "The Measurement of Dielectrics in the Time Domain," *J. of Phys. Chem.*, Vol. 75, No. 3, pp. 616–623 (March, 1969); Hill, et al., *Dielectric Properties and Molecular Behavior*, pp. 108–190, Van Nostrand Reinhold Co. (1969); and Ebert, "Radio Wave Spectra of Sorbed Dipole Molecules," XII. *Collogue Ampere*, pp. 480–484 (1963).

The use of microwave and radio frequency spectroscopy, and particularly reflectivity studies of the dielectric properties of biological materials, either using invasive sampling or in vivo studies, is described in the following articles: Hill, "Human Whole-Body Radio Frequency Absorption Studies Using a TEM-Cell Exposure System," *IEEE Trans. on Microwave Theory and Techniques*, Vol. 30, No. 11, pp. 1847–1853 (November, 1982); Athey, et al., "Measurement of Radio Frequency Permittivity of Biological Tissues with an Open-Ended Coaxial Line: Part I," *IEEE Transactions on Microwave Theory and Techniques*, Vol. MTT-30, No. 1, pp. 82–86 (January, 1982); Stuchly, et al., "Measurement of Radio Frequency Permittivity of Biological Tissues with an Open-Ended Coaxial Line: Part II—Experimental Results," *IEEE Transactions on Microwave Theory and Techniques,* Vol. MTT-30, No. 1, 87–92 (January, 1982); Stuchly, et al., "Coaxial Line Reflection Methods for Measuring Dielectric Properties of Biological Substances at Radio and Microwave Frequencies—A Review," *IEEE Transactions on Instrumentation and Measurement,* Vol. IM-29, No. 3, pp. 176–183 (September, 1980); Burdette, et al., "In Vivo Probe Measurement Technique for Determining Dielectric Properties at VHF Through Microwave Frequencies," *IEEE Transactions on Microwave Theory and Techniques,* Vol. MTT-28, No. 4, pp. 414–427 (April, 1980); and Bianco, et al., "Measurements of Complex Dielectric Constants of Human Sera and Erythrocytes," *IEEE Transactions on Instrumentation and Measurement,* Vol. IM-28, No. 4, pp. 290–295 (December, 1979).

An impedance measurement study is described in Stibitz, et al., "A computer-Aided Bridge for Impedance Measurements in Biological Tissues," *Med. and Bio. Engr.,* pp. 100–104 (Jan., 1974).

Time domain reflectivity studies are somewhat peripheral to the method and apparatus of the present invention since they employ pulses, not a periodic waveform. They are based upon reflection measurements, not directly upon transmission through the target, and they measure permittivity of the target, not the concentration of a selected chemical in the target. The Clark, et al., article entitled "Multiple Reflection Time Domain Spectroscopy" is somewhat more pertinent in that it discloses the use of a subtraction technique in which the reflection signal from a dielectric filled cell is subtracted from the reflection signal of an air-filled cell to minimize the effects of unwanted reflections.

The article by Gestblom, et al. entitled "Transmission Methods in Dielectric Time Domain Spectroscopy" also is pertinent peripherally to the present invention because it is based upon the transmission of an electromagnetic signal through the test sample. Gestblom, et al. use a step pulse generator and compare the transmission of the pulse through the test specimen and through an air-filled coaxial line. Phase shift data are generated, and the dispersion in the test sample is used to measure permittivity. This is again a permittivity study and does not employ a periodic waveform.

The Gestblom, et al., article entitled "A New Transmission Method in Dielectric Time Domain Spectroscopy" discloses both transmission and reflectivity systems in which several one-shot or transient pulses ar employed to enable averaging. The pulses are separated by sufficient time to allow their effects to die out before the next pulse. Empty and filled cells are used and compared.

The Suggett article similarly examines one-shot systems in what is not a real-time technique. FIG. 3 in Suggett includes an amplitude versus frequency plot in the gigahertz range. The experimental error due to a relatively slow rise time, however, make amplitude variations at high frequency essentially insignificant. No attempt to determine concentrations is made using the techniques discussed.

In addition to the pulse studies, transmission studies have been conducted with a single frequency, continuous, periodic, electromagnetic wave in the microwave region. The phase shift and attenuation of the wave during propagation through the test sample have been used to determine various properties of the sample, for example, thickness.

Such single frequency transmission studies, however, have been found to have numerous disadvantages. Accordingly, one approach which has been employed to overcome such disadvantages and to produce more accurate transmission-based microwave spectroscopy data has been to sweep through a range of discrete frequencies in order to generate a time delay spectrum for the frequency or phase-shifts occurring as a result of transmission of microwaves through the target. This approach is disclosed in U.S. Pat. No. 4,135,131 to Larsen, et al.

Larsen, et al. discloses a system in which a sweep generator is employed to sequentially generate a plurality of periodic microwave signals of differing frequency over a range of frequencies. The swept frequencies are in the gigahertz range to maintain the short wavelengths required for the process. The generator output signal is divided and travels in two channels, a reference channel and a test channel. The signal in the test channel is transmitted by an antenna through a target, usually a biological target. A receiving antenna receives the signal after passing through the target, and the received signal is mixed with the reference signal from the reference channel. A detector sums and subtracts the mixed signals, with a low pass filter removing the sums. The differences in amplitude and phase for each of the plurality of sequentially generated signals is passed to a Fourier analyzer, which produces an amplitude versus frequency time delay spectrum for the instantaneous differences of the range of swept frequencies.

The Larsen et al. patent teaches that use of a sequentially swept range of discrete frequencies to produce a time delay spectrum enables a more accurate correlation of time delay to certain characteristics of a test sample than is possible by using previous microwave spectroscopy techniques which employ a single frequency, continuous wave. By generating a time delay spectrum for a series of different frequencies, shifts in the spectrum or pattern of wave attenuation can be calibrated to selected target characteristics, such as thickness, more accurately than a change in phase and amplitude of a wave having single frequency. The Larsen et al. system, for example, is capable of discriminating as to the thickness of brain tissue down to 6 millimeters (about one-quarter inch).

An analyzer somewhat similar to Larsen, et al. is disclosed in the patent to Ghosh et al., U.S. Pat. No. 3,866,118. The Ghosh et al. invention includes a variable frequency microwave generator which is sequentially swept through a plurality of frequencies. Variations in microwave absorption during propagation through known and unknown samples is detected for the various frequencies. These variations are then correlated to the quantity of the chemical being studied. As in Larsen et al., Ghosh et al. employs a sweep generator and produces an absorption spectrum which it correlates to the tested compound.

Microwave resonance also has been employed as a chemical analysis tool. U.S. Pat. Nos. 4,364,008; 4,110,686 and 4,104,585 are based upon the use of microwave resonant cavities. These apparatus measure the shift in frequency of a standing wave. The need to use resonant cavities, however, inherently limits this approach.

U.S. Pat. No. 4,344,440, discloses a continuous wave microwave monitoring apparatus in which a shaped beam is modulated by the electrical activity of a patient's heart or brain. Backscatter radiation is used to monitor the activity of these human organs. U.S. Pat. No. 4,257,001 discloses a microwave-based analyzer which measures the difference in amplitude, frequency, phase or polarization of a polarized microwave field with and without the object to be tested. U.S. Pat. No. 3,265,967, discloses a microwave measuring system for determining the density of a plasma of ions and electrons. The invention employs microwaves in the gigahertz range as a carrier signal and a lower frequency modulation signal. A phase detector is used to measure phase changes produced by the plasma.

Somewhat more peripheral patent art includes U.S. Pat. No. 4,531,526 in which a tuned circuit provides a ring signal in response to microwave irradiation; U.S. Pat. No. 3,051,896 also employing a resonant circuit; and U.S. Pat. No. 4,488,559 directed to a microwave radiometer which measures microwaves emitted from a patient to determine fluid content within various regions of the body.

In an even more general sense, the patent art contains such alternative chemical analysis techniques as nuclear magnetic resonance spectroscopy, U.S. Pat. No. 3,048,772; impedance variation measurements, U.S. Pat. No. 3,287,638; radio frequency alternating magnetic fields, 3,489,522; and conductivity variation measurements, U.S. Pat. No. 3,765,841.

DISCLOSURE OF INVENTION

In accordance with the illustrated preferred embodiment, the present invention provides an apparatus and method for measuring the concentration of a chemical substance in a test sample based upon a technique of transmitting a shaped, periodic, electromagnetic waveform through the target specimen.

It is, therefore, an object of the present invention to provide a spectroscopy apparatus and method which are capable of determining the concentration of a chemical in a test sample.

Another object of the present invention is to provide a radio frequency spectroscopy apparatus and method that are capable of discriminating between a chemical to be tested for and a plurality of different chemicals having similar properties which are contained in the same test sample.

It is another object of the present invention to provide a spectroscopy apparatus and method which are capable of determining the presence and concentration of a selected one of wide range of different chemicals when such selected chemical is present in a relatively chemically complex test specimen.

It is a further object of the present invention to provide a method and apparatus for the non-invasive determination of the concentration of a chemical in a test target or sample.

Another object of the present invention is to provide a spectroscopy apparatus and method which will enable the determination of sodium concentration in a sample.

Still another object of the present invention is to provide a method and apparatus for the determination of chemical properties of a test specimen which is relatively economical to use, can be rapidly accomplished, and is suitable for use by relatively unskilled personnel.

The present invention has other objects and advantages which are set forth in the description of the Best Mode of Carrying out the Invention. The features and advantages described in the specification, however, are not all inclusive, and particularly, many additional features and advantages will be apparent to one of ordinary skill in the art in view of the drawings, specification, and claims herein.

The above objects are achieved by employing an apparatus which includes, briefly, an electromagnetic signal generator which produces a periodic signal, preferably in the radio frequency range, which signal has a shaped waveform, i.e., it is not a sinusoidal signal. The shaped electromagnetic signal from the signal generator has a fundamental frequency or repetition rate plus at least one simultaneously present harmonic frequency. A probe means transmits the signal into the test sample and receives from the test sample a corresponding periodic electromagnetic signal, the waveform of which has been distorted or otherwise transformed by the chemical. A detector circuit quantifies the transformation of the received signal to enable determination of the concentration of the chemical in the test sample.

The method of the present invention includes, briefly, the steps of generating an electromagnetic signal having a shaped, non-sinusoidal periodic waveform, transmitting that signal through the test sample, receiving the signal after it has propagated through the test sample and has been distorted or otherwise transformed by the chemical in the test sample, and detecting the magnitude of the change in shape or transformation of the signal. The magnitude of the change in signal shape then can be correlated to the concentration of the chemical in the test sample. The method of the present invention further involves the tuning of the apparatus for sensitivity to a particular chemical by selecting a repetition rate or fundamental frequency of the shaped waveform and selecting the harmonic frequencies used to produce the shaped waveform. The two selection steps are employed in order to maximize the distortion or change in shape of the transmitted signal due to the presence of the particular chemical being tested for in the test sample. The selection of the repetition rate and waveform shape also facilitates discrimination between the chemical tested for and similar chemicals which are likely to be in the sample.

BRIEF DESCRIPTION OF THE DRAWING

FIG. 1 is a block diagram of a radio frequency spectroscopy apparatus constructed according to the present invention.

FIG. 2 is an enlarged, side elevation view, in cross section of probe assembly utilized in the chemical analysis apparatus of FIG. 1.

FIG. 3 is a schematic diagram of an electronic circuit utilized in the chemical analysis apparatus of FIG. 1 for shaped, periodic signal generation and distortion detection.

FIG. 4 is a schematic diagram of an output circuit utilized in the chemical analysis apparatus of FIG. 1.

FIG. 5 is a curve correlating the voltage output from the analog multiplier of the apparatus of FIG. 3 with the concentration of sodium as present in ionized sodium chloride in water.

BEST MODE OF CARRYING OUT THE INVENTION

The spectroscopy method and apparatus of the present invention are based upon a transmission technique, not upon reflection or resonant cavity approaches. Moreover, a periodic electromagnetic waveform is employed, not a transient one-shot voltage step. Still further, the present invention employs a shaped or non-sinusoidal wave in which a fundamental frequency and at least one harmonic frequency, and usually a plurality of harmonic frequencies, are simultaneously present. It is believed that a combination of simultaneously present sinusoidal frequencies also may produce a shaped waveform which would distort in a manner suitable for use in the method and apparatus of the present invention. The use of a simultaneously present plurality of frequencies differentiates the present invention from prior art approaches such as the Larsen, et al. patent in which a range of discrete frequencies are sequentially employed.

The use of simultaneously present frequencies enables a non-invasive, relatively accurate determination of the concentration of a selected one of a wide range of chemicals in relatively complex test samples. Thus, the concentration of sodium, as it occurs in an ionized form in a solution, can be determined. The present apparatus can be calibrated to provide direct readings of such concentrations. Similarly, the concentration of glucose in blood can be measured without the need for invasive sampling.

FIGS. 1 through 4 of the drawings depict the preferred embodiment of the present invention for purposes of illustration only. One skilled in the art will readily recognize from the following discussion that alternative embodiments of the structures and methods illustrated herein may be employed without departing from the principles of the invention described herein.

The preferred embodiment of the present invention is an apparatus and method for determining the concentration of sodium, as it occurs when sodium chloride exists in an ionized form in an aqueous solution, based on the change in shape of a shaped, periodic, electromagnetic waveform, i.e., by a waveform distortion analysis. As illustrated generally in FIG. 1, the chemical analysis apparatus 10 of the present invention includes a waveform generator 12, a transmitting probe means 14, a receiving probe means 16, a detection circuit 18, and an output device 20. The transmitting and receiving probe means 14 and 16 are preferably placed in contact with a test specimen or sample 22, which here is illustrated as a solution to be tested for the presence and/or concentration of one or more selected chemical substances, such as sodium.

It is broadly known in the transmission-based microwave spectroscopy art, e.g., U.S. Pat. No. 4,135,131 to Larsen, et al., to employ an electromagnetic waveform generator which generates a periodic waveform, a transmitting antenna, a receiving antenna, a detection circuit and output means. The novelty of the apparatus and method of the present invention does not reside in this broad combination.

In order to allow the ability to discriminate between a selected chemical and a background of similar chemicals and in order to have the capability to determine chemical concentrations for a wide range of different chemicals, generator 12 in the present invention is formed to generate or supply a periodic electromagnetic signal having a plurality of simultaneously present frequencies, preferably a fundamental frequency and at least one simultaneously present harmonic frequency. Thus, electromagnetic waveform generator 12 produces a non-sinusoidal or shaped periodic wave, preferably having a fundamental frequency or repetition rate in the range of about one megahertz to about one gigahertz. It is believed, however, that uses for the present apparatus and method in both higher and lower fundamental frequencies will be found.

The method and apparatus of the present invention preferably employs an electromagnetic signal in about the 2 to 4 volt range which produces a field strength of about five to about ten volts per centimeter at the probe assembly. This field strength also is significantly higher than employed, for example, in reflectivity studies using electromagnetic pulses or voltage steps.

The shaped electromagnetic signal 23 is transmitted into the test sample 22, propagates through at least a portion of the test sample, and is received by the receiving probe means 16. The waveform shape and fundamental frequency (repetition rate) of the signal 23 is selected to be susceptible to distortion by the presence of the selected chemical in the test sample in a manner described in detail below. As the shaped signal 23 propagates from transmitting probe means 14 to receiving probe means 16, the signal is changed in shape, distorted or otherwise transformed by the selected chemical substance.

It is hypothesized that the change in shape or distortion of the signal results from one or all of the absorption, backscatter and/or resonance of at least some of the simultaneously present frequencies in the signal with the chemical to be tested. A single, unshaped sine wave at the same fundamental frequency, for example, will undergo little or no distortion in the presence of the test chemical, while the same fundamental periodic wave, when multiple frequencies are present, will undergo sufficient changes in shape to enable the quantified change to be correlated to the concentration of the chemical in the test specimen. Not only can selected harmonics be found which are sensitive to the chemical tested, but changes in concentration of the chemical result in measurably different changes in the waveform shape.

In order to quantify the distortion of the signal transmitted or input to the specimen, both the undistorted or transmitted input signal and the distorted or received output signal are supplied to detection circuit 18, with compares the two signals to determine the magnitude of the distortion or transformation, and generates an output signal based on that comparison. The output signal of detector 18 is supplied to the output device 20, which visually displays the measured concentration of the selected chemical.

FIGS. 2, 3 and 4 illustrate the preferred embodiment of the chemical apparatus of the present invention. Chemical testing apparatus 10 can be adapted to test for the concentration of a wide range of chemicals by varying the fundamental frequency and the waveform shape of the electromagnetic waves produced by generator 12. For the sake of example only, the components in apparatus are set forth below as such apparatus has been constructed to test for the concentration of sodium, as it is present in the form of ionized sodium chloride in water. At a different frequency device 10 also could test for the concentration of chloride. Moreover, the different fundamental frequency responses for similar chemicals, such as ionized potassium chloride in water, indicate that the present apparatus and method has the capability of discriminating between similar chemicals which could be present in the same test sample. It should be understood, that concentration testing in non-aqueous test samples also is possible using the present invention.

FIG. 2 shows probe means 24 in the form of both a transmitting probe 14 and a receiving probe 16. Each probe 14 and 16 is a conductive, cylindrical rod 26 extending outwardly from an insulative housing 28. At the inward end of each rod 26 is an axial cavity 30, into which is soldered a wire 32 that electrically connects rod 26 to either waveform generator 12 or detection circuit 18. Axial cavity 30 was believed originally to provide some filtering effect that was useful, but subsequent use of higher quality oscillators has indicated that probe assembly 24 does not have to have cavity 30. The outward tips of the rods 26 are preferably fully radiused.

As used in this application, the expression "probe means" shall include an assembly which is formed to either contact the sample or to be positioned in near proximity to the sample. It is hypothesized that high frequency conductivity, which requires contact, may play a role in the present invention, although near proximity radiation also is believed to be sufficient. When probe means 24 does not contact the sample and only acts as a radiating antenna, the sensitivity of the apparatus must increase with the increasing distance between the probe means and the sample.

In FIG. 3, the circuitry of detection circuit 18 is illustrated. The heart of detection circuit 18 is an analog multiplier 34, which receives both the transmitted and received signals as input signals and generates an output signal that is related to the amount of change in shape or distortion in the transmitted signal that is caused by the selected chemical, for example, sodium.

In the preferred embodiment, waveform generator 12 is a square wave generator 36, which is coupled to a Y input terminal of analog multiplier 34 through a capacitor 38, and is coupled to transmitting probe 14 of probe means 24 through capacitor 40. Receiving probe 16 of probe means 24 is coupled to an X input terminal of analog multiplier 34 through a capacitor 42. Capacitors 40 and 42 isolate probe means 24 from any direct current components of signal 23 and block direct current flow to the X input terminal. Capacitor 38 blocks direct current input to the Y input terminal. Resistors 44 and 48 provide a stable bias point into the X and Y inputs.

The capacitor and resistor network includes capacitor 38 and a resistor 44 connected between the Y input terminal and a grounded node 46, and capacitor 42 and a resistor 48 connected between the X input terminal and the grounded node 46. In order to provide a high frequency ground, a resistor 50 and a capacitor 52 are connected in parallel between the common input terminal and the grounded node 46.

The analog multiplier 34 in effect quantifies the amount of distortion or the change in shape between the shaped transmitted, signal and the distorted received signal, which change in shape is directly related to the concentration of sodium ions in test sample 22.

As used in this application the expression "distortion" shall mean a change in amplitude phase or slope of the waveform in the time domain. Detection circuit 18 measures changes in amplitude and phase between the transmitted and received signals. Since the repetition rate or fundamental frequency of the shaped waveform has been found to remain the same in the tests conducted thus far, it would appear that the distortion occurs as a result of the change in amplitude and/or frequency of the harmonic frequencies used to shape the wave. It should be noted, that the frequency also can be distorted.

The analog multiplier 34 multiplies the differential voltage applied across the X input and common terminals by the differential voltage applied across the Y input and common terminals. Since the reference signal supplied by the capacitor and resistor network is intermediate in voltage between the transmitted and received signals, one differential input to analog multiplier 34 is positive and the other is negative. Thus, the X times Y product output signal is inversely related to the difference between the transmitted and received signals, and is, thus, inversely related to the concentration of sodium ions in test sample 22.

The output signal of analog multiplier 34 is conditioned and then supplied to output device 20. A capacitor 54 smooths the pulses and irregularities in the output signal of analog multiplier 34 to supply a stable, direct current signal to a buffer 56. The output terminal of buffer 56 is coupled to ground through a resistor 58 and to the inverting input terminal of an operational amplifier 60 through another resistor 62. Operational amplifier 60 is configured as an inverting amplifier with a reference voltage, Vref, supplied to its non-inverting input terminal, and a resistor 64 coupled to feedback the output, Vout, to the inverting input terminal. Since operational amplifier 60 is configured as an inverting amplifier, the output signal of the operational amplifier 60, Vout, is directly related to the concentration of sodium ions in test sample 22.

As shown in FIG. 4, output device 20 receives the output signal of operational amplifier 60, Vout, and, if the measured concentration of sodium ions is high enough, activates one of five light emitting diodes 66. Output device 20 includes a non-inverting operational amplifier 68, and five operational amplifiers 70 configured as comparators. An adjustable resistor 72 is connected to feedback the output of operational amplifier 68 to its inverting input terminal, which also is coupled to ground through a resistor 74. The output signal of detection circuit 18, Vout, is supplied to the non-inverting input terminal of the operational amplifier 68. The output terminal of operational amplifier 68 is connected to the inverting input terminals of the five comparator operational amplifiers 70.

A resistor ladder 76 consisting of six resistors 78, 80, 82, 84, 86, and 88 is coupled between a supply voltage, Vs, and ground. Each of the five internal nodes of resistor ladder 76 is connected to the non-inverting input terminal of one of comparator operational amplifiers 70. Resistors 90, 92, 94, 96, and 98 are connected as feedback resistors between the output terminal of each comparator operational amplifier 70 and its non-inverting input terminal. A resistor and diode ladder 100 consisting of six resistors 102, 104, 106, 108, 110, and 112 and six diodes 66 and 114 is coupled between the supply voltage and ground. Each of the five internal nodes of the resistor and diode ladder 100 is connected to the output terminal of one of comparator operational amplifiers 70. The output terminals of four of the comparator operational amplifiers 70 are coupled to the supply voltage via pull-up resistors 116, 118, 120, and 122, respectively.

The output signal of operational amplifier 68 acts in cooperation with resistor ladder 76 and comparator operational amplifiers 70 to turn on the appropriate light emitting diode (LED) 66. Assume, for example, that the output voltage of the operational amplifier 68 is less than the voltage at the node between resistors 80 and 82, but greater than the voltage at the node between resistors 82 and 84. This will cause the upper two comparator operational amplifiers 70 to supply positive output voltages, while causing the lower three comparator operational amplifiers 70 to supply negative output voltages. Current will flow through resistor 106, causing the middle LED 66 to light. The other LED's 66 will not light because no current will flow through resistors 102, 104, 108, and 110.

As will be appreciated, a greater or lesser number of LED's can be employed in output device 20, depending upon the application to which the present apparatus is put. Moreover, analog or digital output displays can be coupled to detector 18 if desired. The illustrated output device 20 is suitable for use for detecting sodium in food and can be embodied in a relatively inexpensive instrument suitable for use by untrained users as a simple but accurate device for monitoring the sodium content of their food.

In order to tune the sensitivity of the present apparatus to a selected chemical such as sodium, the waveform shape and the fundamental frequency or repetition rate of the transmitted signal are both selected so that the distortion or transformation of the signal is particularly responsive to the presence of the selected chemical. Obviously, the harmonic frequencies by definition will be related to the fundamental frequency selected, but both the waveform shape (harmonics) and the waveform frequency (fundamental) can be tuned to particular chemicals and used to accurately discriminate between closely related chemicals.

The process of selecting the fundamental and harmonic frequencies used to produce the shaped wave of the apparatus of the present invention can be accomplished empirically and, to some extent ca be assisted by calculations. It is believed that eventually the selection process may be susceptible in its entirety to mathematical analysis techniques.

The first step in the empirical selection process is to determine at which fundamental frequencies a chemical substance causes a maximum amount of distortion in a shaped wave. A square wave is a desirable form of shaped wave because it contains a broad spectrum of harmonic frequencies. A square wave has been found to exhibit at least some change in shape when transmitted through wide range of different chemicals. The probe means is inserted into a test sample containing a known amount of the selected chemical substance. Then, the distortion of the square wave signal is monitored while varying the fundamental frequency or repetition rate of the square wave signal sequentially through a range of frequencies, typically between about one megahertz and to about one gigahertz. As the repetition rate is changed, the square wave generator automatically correspondingly varies the harmonics required to maintain the square waveform. The distortion of the square wave can be monitored by examining the output signal of the analog multiplier, or by displaying the Lissajous patterns of the analog multiplier differential input signals on an oscilloscope and looking for complex or distorted patterns.

Most likely, several fundamental frequencies will produce peaks in the magnitude of the distortion of the square wave signal. It is advantageous to repeat the above process for several of the chemical substances most likely to be found in test samples in company with the selected chemical substance. Some of the fundamental frequency peaks of the companion substances may approach or coincide with some of the fundamental frequency peaks of the selected substance. By choosing a fundamental frequency peak for the selected substance which is isolated or separated from frequency peaks for the companion chemicals, interference and false readings due to the companion substances will not occur. It has been found that square wave signals at a frequency of about sixteen megahertz is a good choice for the measurement of concentrations of sodium ions in an aqueous solution.

Once a fundamental frequency is selected, the waveform shape of the transmitted signal can be varied by changing the simultaneously present harmonic frequencies to investigate whether waveform shapes other than a square wave are more susceptible to distortion by the chemical substance.

In addition to simply empirically testing various waveform shapes, the selection of the waveform shape can be based in part upon the results of the selection process for the fundamental frequency. Since the selection of the fundamental frequency preferably is accomplished by using a waveform rich in harmonics, there typically will be a band of frequencies showing distortion around the frequency at which the most distortion occurs. If a shaped wave is employed which includes harmonics in this band, there is a tendency to obtain further enhancement of the distortion sensitivity to the chemical.

It has been found that Fourier analysis can be used to calculate which frequencies are likely to produce a high degree of waveform distortion. A Fourier analysis of a proposed waveform will reveal a clustering of the harmonic frequencies used to shape the wave at certain frequencies which correspond to the frequencies at which substantial distortion occurs during empirical testing. Thus, if the harmonics cluster at frequencies which are also resonant fundamental frequencies for the chemical being empirically tested, use of such a waveform shape will be likely to produce the desired shape changes upon transmission of the waveform through the specimen.

Moreover, once an alternative waveform is selected which produces greater or about equal distortion to the distortion resulting from a square wave, the fundamental frequency should be varied for the new waveform to determine whether or not an even more sensitive and selective fundamental frequency may exist for the new waveform. One can try multiples (harmonics) of a sensitive frequency as the fundamental frequency during the fundamental frequency selection process.

As the chemicals tested for and the samples in which they occur become more complex, it is believed that discrimination between chemicals may require the use of combinations of signals. Thus, the distortion of a square wave at 20 megahertz might be added to the distortion measured for a pulsed ramp waveform at 10 megahertz to determine the concentration of an organic chemical in a complex sample. The use of combined signals has not been fully investigated. The goal in this process, in any event, is to select a shaped signal, or combination of shaped signals, that is distorted by the presence of the selected chemical substance, but is not distorted by the presence of companion chemical substances that also may be in the test sample. Moreover, it is preferable that the quantity of distortion can be correlated to the concentration of the chemical.

In addition to selecting the waveform shape and repetition rate of the transmitted signal, the component values of the capacitor and resistor network also may be selected to improve the signal to noise ratio of the apparatus for the particular chemical. This selection process also may be empirical, and should be coordinated with the selection of the transmittal signal. Again, the distortion can be monitored by examining the output signal of the analog multiplier, or by displaying the Lissajous patterns of the analog multiplier differential input signals on an oscillosoope and looking for complex or distorted patterns. Generally, balanced X and Y inputs will give better sensitivity.

EXAMPLES

The following table lists the component values of the capacitors and resistors employed in apparatus constructed in accordance with the present invention and used to measure the concentration of sodium ions in water:

| | |
|---|---|
| capacitors 38, 40, 42 | 0.01 microfarad |
| resistor 44 | 2000 ohm |
| resistor 50 | 1000 ohm |
| capacitor 52 | 0.68 microfarad |
| capacitor 54 | 2.2 microfarad |
| resistor 58 | 5100 ohm |
| resistor 62, 64 | 100,000 ohm |
| resistor 72 | 5000 ohm, variable |
| resistor 74 | 1000 ohm |
| resistor 78 | 22,000 ohm |
| resistor 80 | 4700 ohm |
| resistor 82 | 8200 ohm |
| resistor 84 | 12,000 ohm |
| resistor 86 | 8200 ohm |
| resistor 88 | 24,000 ohm |
| resistor 90, 92, 94, 96, 98 | 470,000 ohm |
| resistor 102 | 470 ohm |
| resistor 104 | 820 ohm |
| resistor 106, 108, 110, 112 | 470 ohm |
| resistor 116, 118, 120, 122 | 10,000 ohm |

The distance between probe elements 14 and 16 was set at 0.80 inches. The areas of the probe elements were too small to reliably calculate the spacing that would produce the best efficiency, but signal peaks were observed at several spacings as the elements 14 and 16 were separated. The selected spacing was believed to be a fractional multiple of the transmission fundamental frequency which would enhance efficiency, although other spacings are acceptable in connection with the apparatus and method of the present invention.

FIG. 5 illustrates the output voltage, measured between the X times Y product output signal and the reference voltage, $V_{REF}$, as the concentration of sodium is increased in 100 milliliters of water. As will be seen, the curve would essentially be a straight line if plotted on a logarithmic scale. It was found that extremely high reproduceability could be achieved in connection with these data, making it possible to accurately detect the presence of sodium ions and their concentration in milligrams per 100 milliliters of solution.

The curve of FIG. 5 was generated by employing a square wave signal transmitted at 16 megahertz with a voltage level of about four volts. Empirical testing revealed that sodium chloride ionized in water exhibited frequency peaks at 16, 17.75, and 42.50 megahertz, with the greatest distortion occurring at 17.75 megahertz. Potassium chloride ionized in water exhibits frequency peaks at 17.75 and 35.70 megahertz. Potassium chloride is a frequent substitute for sodium chloride in food products to avoid the deleterious effects of sodium. Accordingly, in order to discriminate between the undesirable sodium ion and the acceptable potassium ion, 16 megahertz was chosen instead of the common 17.75 megahertz frequency.

If one wanted to sense the presence of either sodium chloride or potassium chloride, a transmitter operating at 17.75 could be employed. Since both potassium chloride and sodium chloride exhibit significant distortion at 18 megahertz, a commercially available 18 megahertz transmitter also would give good results. If the distortion sensitivity drops off rapidly with frequency change, however, use of the precise frequency at which significant distortion occurs should be made. Volume, of course, makes even custom transmitters economically feasible.

As will be apparent, it also would be possible to use paired oscillators for greater selectivity as to the ion being sensed.

The sodium ion detector also was used with vinegar, sugar, alcohol and various starch solutions and accurately produced outputs indicating that there was no sodium present. It did not, therefore, give false positive readings in such solutions, including heavily ionized solutions.

When mixtures of sodium chloride and vinegar, sugar, starch, etc. were measured, the apparatus of the present invention could sense the presence and accurately measure the concentration of sodium chloride in such solutions.

Using the method of the present invention, sensitive fundamental frequencies were also obtained for water test solution containing potassium chloride, sugar, alcohol, and vinegar. Water also was tested and the sensitive fundamental frequency found. The component values of the capacitors and resistors for the sodium ion detector remained the same, and following distortion sensitive fundamental frequencies were found for a four volt square wave:

| Compound | Fundamental Frequency (Megahertz) |
|---|---|
| Potassium Chloride | 16, 17.75, 42.50 |
| Potassium Chloride | 17.75, 37.70 |
| Sugar | 44.3, 44.6, 50.0 |
| Vodka | 16.62, 35.5, 35.95 |
| Vinegar | 20.4 |
| Water | 19.80, 32.05, 35.6 |
| | 36.31, 44.3, 50.0 |

In connection with the sodium testing a tilt waveform also has been used. A tilt has the shape of a square wave except the amplitude after the initial rise slopes or tilts in a downward direction instead of remaining constant across the wave. A tilt waveform was found to distort with the most sensitivity at 14 megahertz.

Similarly, a pulsed ramp waveform was used to test ethyl alcohol. A pulsed ramp waveform rises from zero on a slope to a maximum amplitude, falls to zero and remains at zero for the second one-half of the cycle. A pulsed ramp distorted at 11.5 megahertz for ethyl alcohol.

In solution and non-invasive blood glucose concentrations have been determined using the apparatus and method of the present invention. Probe means 28 can be as shown in FIG. 2 for solution and gel testing. For non-invasive tests probe means 28 preferably takes the form of a recess dimensioned to receive the pad on the end of the patient's finger. A transmitting probe element and a receiving probe element contact the patient's skin at about 45 degree angles with respect to the horizontal (a 90 degree included angle between the probe elements). The probe elements are separated from each other at the surface of the finger receiving recess by about 5/16 inches. A non-reactive film, such as a co-polymer of vinyl chloridevinylidene chloride (0.4 mil film sold under the trademark SARAN), can be positioned in the recess over the probe elements to enhance the uniformity of transmission of the signal through the patient's finger.

Testing of blood in solutions and gels and Fourier calculations have revealed that a four volt pulsed ramp waveform at fundamental frequencies of 10 and 15 megahertz were most sensitive. Moving from a square wave to a pulsed ramp waveform enhanced the sensitivity by a factor of about 10.

In vivo testing was conducted in which a patient held his finger firmly, but without great pressure or effort, in the probe assembly recess with the non-reactive film between the probes and finger. A square wave generator was used with a four volt output at 30 megahertz (twice the solution testing fundamental of 15 megahertz for a pulsed ramp). Measurements were taken every 15 minutes for ten hours. The concentrations measured were correlated to the in solution tests. It was found that blood glucose levels in the range of about 50 to about 150 milligram percent were measured. Moreover, the changes in level tracked closely food intake during the period. As the glucose level exceeds 110 milligram percent retuning of the apparatus is helpful and may be required for a high degree of accuracy.

It is believed that the 50 to 150 milligram percent range can be increased by further refinement of the test apparatus and method.

The apparatus and method of the present invention also appear to be well suited for computer implementation to perform complex chemical analyses. A rapid series of shaped signals at selected fundamental frequencies tuned to selected chemicals can be sequentially transmitted with corresponding circuit variations, if required, to enable a high degree of selectivity and a large range of chemical compounds to be sensed, measured, stored and then output using the apparatus of the present invention and a microprocessor controller.

From the above description, it will be apparent that the invention disclosed herein provides a novel and advantageous apparatus and method for determining chemical concentration based on shaped waveform distortion analysis. The foregoing discussion discloses and describes merely exemplary methods and embodiments of the present invention. One skilled in the art will readily recognize from such discussion that various changes, modifications and variations may be made therein without departing from the spirit and scope of the invention. Accordingly, the disclosure of the present invention is intended to be illustrative, but not limiting, of the scope of the invention, which is set forth in the following claims.

We claim:

1. In an apparatus enabling a determination of the concentration of a chemical in a test sample including electromagnetic waveform generation means for generating a electromagnetic signal, probe means coupled to said generation means for transmission of said signal as an input signal into said test sample and formed for receipt of said signal after propagation through at least a portion of said test sample as an output signal, and detection means coupled for receipt of said input signal and said output signal and responsive thereto to quantify a change between said input signal and said output signal, the improvement in said apparatus comprising:

said generation means generating a periodic electromagnetic signal having plurality of simultaneously present frequencies to produce a periodic waveform of known shape; and said detection means being responsive to said input signal and said output signal to quantify a change in shape between said input signal and said output signal.

2. The apparatus as defined in claim 1 wherein, said generation means generates a periodic electromagnetic signal having a fundamental frequency and at least one simultaneously present harmonic frequency to produce a non-sinusoidal waveform.

3. The apparatus as defined in claim 1 wherein, said detection means further is responsive to said input signal and said output signal to correlate the quantified change in shaped with a concentration of said chemical in said sample.

4. The apparatus as defined in claim 1 wherein, said generation means generates a periodic electromagnetic signal having a fundamental frequency in the range of one megahertz to one gigahertz.

5. The apparatus as defined in claim 4 wherein, said generation means generates a signal having a field strength at said probe means of about 5 to about 10 volts per centimeter.

6. The apparatus as defined in claim 1 wherein, said generator means generates a signal having a fundamental frequency selected to be one of:
(a) 10 megahertz and multiples thereof; and
(b) 15 megahertz and multiples thereof.

7. The apparatus as defined in claim 1 wherein, said generation means generates a periodic electromagnetic signal having broad spectrum of harmonic frequencies.

8. The apparatus as defined in claim 7 wherein, said generation means generates one of a square wave and pulsed ramp waveform signal.

9. In a radio frequency spectroscopy apparatus including a radio frequency generator generating a periodic electromagnetic signal in the one megahertz to one gigahertz range, electromagnetic signal transmission means coupled to said generator for receipt of said signal therefrom and transmitting said signal into a test sample, electromagnetic signal receiving means receiving said signal after propagation through at least a portion of said test sample, and detection means coupled to receive said signal as transmitted into said sample and coupled to receive said signal as received from said sample, said detection means response to the transmitted signal and the received signal to produce an output quantifying a change therebetween, the improvement in said apparatus comprising:

said generator generating a periodic waveform of non-sinusoidal shape; and said detection means being responsive to the transmitted signal and the received signal to quantify any distortion of said periodic waveform as a result of transmission through said test sample.

10. In a method for detecting the presence of a chemical in a test sample including the steps of transmitting a periodic electromagnetic signal through a portion of said test sample, receiving said signal after propagation through said test sample, and quantifying any difference between the transmitted signal and the received signal, the improvement in said method comprising:

during said transmitting step, transmitting a periodic signal having at least two frequencies simultaneously present to produce a shaped periodic waveform; and during said quantifying step, quantifying any distortion of said waveform as a result of propagation through said test sample.

11. The method as defined in claim 10 wherein,
during said transmitting step, transmitting a signal having a fundamental frequency and at least one simultaneously present harmonic frequency.

12. The method as defined in claim 10 wherein,
during said transmitting step, transmitting a signal having harmonic frequencies selected to be sensitive to the presence of said chemical in said test sample to produce a sufficient change in shape of said signal during propagation through said test sample to enable correlation of said change in shape to concentration of said chemical in said test sample.

13. A method of selecting an electromagnetic signal having a waveform useful in a transmission spectroscopy process to determine the concentration of a chemical in test sample comprising the steps of:

transmitting a periodic electromagnetic signal having a waveform with a fundamental frequency and a broad based of harmonic frequencies simultaneously present to shape said waveform through a test sample containing said chemical;

sequentially transmitting signals through said test sample having substantially the same waveform shape and different fundamental frequencies over a range of frequencies;

detecting any distortion of said signals over said range of frequencies resulting from transmission of said signals through said sample; and selecting a signal having a frequency which is a multiple of a frequency for which significant waveform distortion was detected during said detecting step.

14. The method as defined in claim 13 wherein,
said transmitting step is accomplished by transmitting one of a square wave and a pulsed ramp wave through said test sample.

15. The method as defined in claim 13,
after said selecting step, varying the waveform shape of said signal at said selected frequency;

detecting any increase in waveform distortion compared to distortion detected for said same waveform shape; and selecting a signal having a waveform shape exhibiting an increased distortion as compared to said same waveform shape.

16. The method as defined in claim 15, and
after said step of selecting said waveform shape, sequentially varying the fundamental frequency of said signal through a range of frequencies while maintaining said selected waveform shape;

detecting any increase in distortion during said last step of varying the fundamental frequency; and selecting a fundamental frequency for said signal having a greater distortion than said fundamental frequency first selected for said signal.

17. The method as defined in claim 13 wherein,
said signals having a frequency in the range of one megahertz and one gigahertz are transmitted during said transmitting steps.

* * * * *